(12) United States Patent
Leung (10) Patent No.: US 6,440,386 B1
(45) Date of Patent: Aug. 27, 2002

(54) STABILIZED RADIOPHOSPHATE-LABELED PROTEINS

(75) Inventor: Shui-on Leung, Morris Township, NJ (US)

(73) Assignee: Immunomedics, Inc., Morris Plains, NJ (US)

(*) Notice: Subject to any disclaimer, the term of this patent is extended or adjusted under 35 U.S.C. 154(b) by 0 days.

(21) Appl. No.: 09/347,926

(22) Filed: Jul. 6, 1999

Related U.S. Application Data (60) Provisional application No. 60/091,736, filed on Jul. 6, 1998.

(51) Int. Cl.[7] .................. A61K 51/00; A61M 36/14; C07K 16/00; C12P 21/08
(52) U.S. Cl. .................. 424/1.53; 424/1.69; 424/1.77; 424/178.1; 424/179.1; 530/391.3; 530/391.5
(58) Field of Search .................. 424/178.1, 179.1, 424/1.53, 1.69, 1.77; 530/391.3, 391.5

(56) References Cited

U.S. PATENT DOCUMENTS

| | | | | |
|---|---|---|---|---|
| 5,352,660 A | | 10/1994 | Pawson et al. | 514/12 |
| 5,667,980 A | | 9/1997 | Pawson et al. | 435/7.8 |
| 5,786,454 A | * | 7/1998 | Waksman | |
| 6,146,628 A | * | 11/2000 | Uckun et al. | |

OTHER PUBLICATIONS

Foxwell et al, "Conjugation of monoclonal antibodies to a synthetic peptide substrate for protein kinase", British Journal of Cancer, 1988, vol. 57, pp. 489–493.*

Brunati et al, "Src homology–2 domains protect phosphotyrosyl residues against enzymatic dephosphorlation", Biochemical and Biophysical Research Communications, 1998, vol. 243, pp. 700–705. (abstract).*

Scharenburg et al, "Reconsitution of interactions between tyrosine kinases and the high affinity IgE recptor", EMBO, 1995, vol. 14, pp. 3385–3394. (abstract).*

Gervais et al, "The SH2 domain is required for stable phosporylation of the p56lck at tyrosine 505", Molecular and Cellular Biology, 1993, vol. 13, pp. 7112–7121. (abstract).*

Cobb et al, "Stable association of pp60src and pp59fyn with the foacl adhesion–associated protein tyrosine kinase, pp125FAK", Molecular and Cellular Biology, 1994, vol. 14, pp. 147–155. (abstract).*

Rotin et al, "SH2 domains prevent tyrosine dephosphorylation of the EGF receptor", EMBO, 1992, vol. 11, pp. 559–567. (abstract).*

Harris, "Production of humanized monoclonal antibodies for in vivo imaging and therapy", Biochemical Society Transactions, 1995 vol. 23, pp. 1035–1038.*

A.M. Creighton et al., "The Development of $^{32}$P technology for radioimmunotherapy" Chapter 11 of Monoclonal Antibodies 2, Application is clinicaly oncology, 1993, pp. 103–109.

Shi–on Leung et al., "Bacterial Expression of a Kemptide Fusion Protein Facilities . . . Antibody Fragment", Cancer Res. (Supp), 12/95, pp. 5968s–5972s.

Z. Songyang et al., "SH2 Domains Recognize Specific Phosphopeptide Sequences", Cell, vol. 72, 3/93, pp. 767–778.

\* cited by examiner

Primary Examiner—Anthony C. Caputa
Assistant Examiner—Karen A. Canella
(74) Attorney, Agent, or Firm—Foley & Lardner (57) ABSTRACT

A radiotherapeutic agent comprising a $^{32}$P or $^{33}$P radiolabeled protein selected from the group consisting of:

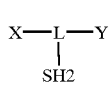

(IV)

wherein X is an targeting peptide, Y is a phosphorylation peptide, L is a flexible linker, preferably a peptide linker, and SH2 represents an SH2 domain; whereby said phosphorylation peptide is radiolabeled with $^{32}$P or $^{33}$P

25 Claims, 2 Drawing Sheets

Figure 1

SEQUENCE LISTING

<160> NUMBER OF SEQ ID NOS: 24

<210> SEQ ID NO 1
<211> LENGTH: 23
<212> TYPE: PRT
<213> ORGANISM: Homo sapiens

<400> SEQUENCE: 1

Pro Gln Glu Gly Leu Tyr Asn Glu Leu Gln Lys Asp Lys Met Ala Glu
 1               5                  10                  15

Ala Tyr Ser Glu Ile Gly Met
            20

<210> SEQ ID NO 2
<211> LENGTH: 11
<212> TYPE: PRT
<213> ORGANISM: Homo sapiens

<400> SEQUENCE: 2

Asn Leu Ser Lys Arg Tyr Glu Glu Ile Tyr Leu
 1               5                  10

<210> SEQ ID NO 3
<211> LENGTH: 11
<212> TYPE: PRT
<213> ORGANISM: Homo sapiens

<400> SEQUENCE: 3

Glu Gly Asp Glu Ile Tyr Glu Asp Leu Met Arg
 1               5                  10

<210> SEQ ID NO 4
<211> LENGTH: 11
<212> TYPE: PRT
<213> ORGANISM: Homo sapiens

<400> SEQUENCE: 4

Ala Ser Glu Gln Gly Tyr Glu Glu Met Arg Ala
 1               5                  10

<210> SEQ ID NO 5
<211> LENGTH: 11
<212> TYPE: PRT
<213> ORGANISM: Homo sapiens

<400> SEQUENCE: 5

Glu Leu Gln Asp Asp Tyr Glu Asp Met Met Glu
 1               5                  10

<210> SEQ ID NO 6
<211> LENGTH: 11
<212> TYPE: PRT
<213> ORGANISM: Homo sapiens

<400> SEQUENCE: 6

Ala Ala Cys Val Val Tyr Glu Asp Lys Ser His
 1               5                  10

<210> SEQ ID NO 7
<211> LENGTH: 11
<212> TYPE: PRT
<213> ORGANISM: Homo sapiens

```
<400> SEQUENCE: 7

Pro Ile Ala Ser Lys Tyr Glu Asp Met Tyr Pro
 1               5                  10

<210> SEQ ID NO 8
<211> LENGTH: 12
<212> TYPE: PRT
<213> ORGANISM: Homo sapiens

<400> SEQUENCE: 8

Glu Glu Glu Gly Glu Gly Tyr Glu Glu Pro Asp Ser
 1               5                  10

<210> SEQ ID NO 9
<211> LENGTH: 12
<212> TYPE: PRT
<213> ORGANISM: Homo sapiens

<400> SEQUENCE: 9

Ser Gln Asp Gly Ser Gly Tyr Glu Asn Pro Glu Asp
 1               5                  10

<210> SEQ ID NO 10
<211> LENGTH: 12
<212> TYPE: PRT
<213> ORGANISM: Homo sapiens

<400> SEQUENCE: 10

Asp Asp Gly Glu Ile Thr Tyr Glu Asn Val Gln Val
 1               5                  10

<210> SEQ ID NO 11
<211> LENGTH: 12
<212> TYPE: PRT
<213> ORGANISM: Homo sapiens

<400> SEQUENCE: 11

Asp Arg Arg Glu Arg Asp Tyr Thr Asn Leu Pro Ser
 1               5                  10

<210> SEQ ID NO 12
<211> LENGTH: 12
<212> TYPE: PRT
<213> ORGANISM: Homo sapiens

<400> SEQUENCE: 12

Pro Glu Pro Pro Pro Val Tyr Thr Asn Leu Ser Ser
 1               5                  10

<210> SEQ ID NO 13
<211> LENGTH: 12
<212> TYPE: PRT
<213> ORGANISM: Homo sapiens

<400> SEQUENCE: 13

Glu Phe Ala Gly Phe Ser Tyr Thr Asn Pro Glu Phe
 1               5                  10

<210> SEQ ID NO 14
<211> LENGTH: 12
<212> TYPE: PRT
<213> ORGANISM: Homo sapiens

<400> SEQUENCE: 14
```

```
Ala Lys Ile Leu Lys Gln Tyr Asp His Pro Asn Ile
 1               5                  10
```

<210> SEQ ID NO 15
<211> LENGTH: 12
<212> TYPE: PRT
<213> ORGANISM: Homo sapiens

<400> SEQUENCE: 15

```
Pro Leu Cys His Ser Asp Tyr Asp Glu Asp Asp Tyr
 1               5                  10
```

<210> SEQ ID NO 16
<211> LENGTH: 12
<212> TYPE: PRT
<213> ORGANISM: Homo sapiens

<400> SEQUENCE: 16

```
Phe Leu Pro Val Pro Glu Tyr Ile Asn Gln Ser Val
 1               5                  10
```

<210> SEQ ID NO 17
<211> LENGTH: 12
<212> TYPE: PRT
<213> ORGANISM: Homo sapiens

<400> SEQUENCE: 17

```
Ala Val Gly Asn Pro Glu Tyr Leu Asn Thr Val Gln
 1               5                  10
```

<210> SEQ ID NO 18
<211> LENGTH: 12
<212> TYPE: PRT
<213> ORGANISM: Homo sapiens

<400> SEQUENCE: 18

```
Leu Phe Asp Asp Pro Ser Tyr Val Asn Val Gln Asn
 1               5                  10
```

<210> SEQ ID NO 19
<211> LENGTH: 22
<212> TYPE: PRT
<213> ORGANISM: Homo sapiens

<400> SEQUENCE: 19

```
Glu Ser Asp Gly Gly Tyr Met Asp Met Ser Lys Asp Glu Ser Val Asp
 1               5                  10                  15

Tyr Val Pro Met Leu Asp
                 20
```

<210> SEQ ID NO 20
<211> LENGTH: 11
<212> TYPE: PRT
<213> ORGANISM: Homo sapiens

<400> SEQUENCE: 20

```
Asp Ser Thr Asn Glu Tyr Met Asp Met Lys Pro
 1               5                  10
```

<210> SEQ ID NO 21
<211> LENGTH: 12
<212> TYPE: PRT
<213> ORGANISM: Homo sapiens

<400> SEQUENCE: 21

```
Asn Glu Gly Asp Asn Asp Tyr Ile Ile Pro Leu Pro
  1               5                  10

<210> SEQ ID NO 22
<211> LENGTH: 15
<212> TYPE: PRT
<213> ORGANISM: Homo sapiens

<400> SEQUENCE: 22

Arg Cys Ile Asn Tyr Val Phe Phe Pro Ser Leu Lys Pro Ser Ser
  1               5                  10                  15

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Peptide
      linker

<400> SEQUENCE: 23

Gly Gly Gly Ser Gly Gly Gly Ser Gly Gly Gly Ser Gly Gly Gly Ser
  1               5                  10                  15

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

His Thr Cys Pro Pro Cys Pro Arg Cys Ile Asn Tyr Val Phe Phe Pro
  1               5                  10                  15

Ser Leu
```

STABILIZED RADIOPHOSPHATE-LABELED PROTEINS

This application claims the benefit of provisional application 60/091,736 filed Jul. 6, 1998.

BACKGROUND OF THE INVENTION

The present invention relates to phosphorus-32 and phosphorus-33 labeled proteins which are useful for radiotherapy of human diseases. In particular, the invention relates to proteins which contain peptide sequences that are substrates for protein kinase enzymes, and that can be radiolabeled with a protein kinase and a $^{32}$P or $^{33}$P-labeled phosphate donor and contain an SH2 domain which serves to protect the phosphorylated protein from in vivo dephosphorylation. This invention also relates to a method of therapy using the radiolabeled proteins.

Many radionuclides have been studied for their suitability for internal administration to patients in radiotherapy. Some radionuclide compounds, containing isotopes such as $^{131}$I, can be given systemically, taking advantage of the fact that these elements tend to localize to particular tissues by virtue of their chemical properties. Other radionuclides, such as $^{198}$Au and $^{103}$Pd have been administered in a localized fashion, for instance to the site of a tumor. Most recent approaches, however, have focused on methods of delivering radionuclides to a preselected tissue by attaching the radionuclide to a targeting protein, usually an antibody, which will then localize to that tissue.

A large number of methods for associating radionuclides to antibodies have been developed. The chemical toxicity of many radionuclides means that complex methods must often be used to stably bind the isotope to an antibody. For example, to use $^{90}$Y, which has many desirable radiochemical properties, a chelate must be synthesized and covalently bound to the antibody to stably link the radioisotope to the antibody.

Currently there are isotopes which have been utilized in radiolabeled agents and include $^{131}$I, $^{90}$Y, $^{188}$Re, $^{186}$Re, $^{67}$Cu, and $^{212}$Pb/$^{212}$Bi. Each has significant, sometimes multiple, disadvantages including low-energy particle emissions, such as $^{131}$I and $^{67}$CU; severe organ toxicity, such as $^{90}$Y and $^{212}$Pb/$^{212}$Bi; short half-life for radioimmunotherapy, such as $^{188}$Re and $^{212}$Pb/$^{212}$Bi; high gamma-energy emissions, such as $^{131}$I; low specific activity, such as $^{186}$Re; non-amenability to out-patient procedures, such as $^{131}$I, $^{67}$Cu and $^{212}$Pb/$^{212}$Bi and supply and/or cost concerns, such as $^{188}$Re, $^{186}$Re, $^{67}$Cu, and $^{212}$Pb/$^{212}$Bi.

One isotope which has received little attention, due to the difficulty of the chemistry involved in linking it to antibodies, but otherwise displays desirable properties for radioimmunotherapy is $^{32}$P. $^{32}$P is inexpensive, is readily available in high specific activity in a variety of labeled molecules, and has a therapeutically desirable half-life of 14 days. Additionally, it has been previously used clinically, has no gamma emissions, is carrier-free and has an intense beta-emission. It is absorbed by the body and is not readily excreted, and is therefore amenable to use in outpatient procedures. In addition, $^{32}$P emits only β-radiation with an excellent depth penetration in tissue of approximately 6 mm. Unlike many other radionuclides under consideration for targeted radiotherapy, it is not inherently toxic, and is currently used clinically in some non-targeted applications, for example, for the treatment of ovarian cancer and polycythemia rubra vera.

Another radioisotope of phosphorus, $^{33}$P, has received even less attention than $^{32}$P. $^{33}$P shares the same chemical properties as $^{32}$P, and has similarly desirable radiochemical characteristics. It is available in high specific activity, and has a 25-day half life with a β-particle emission energy of 0.25 MeV, approximately 15% of the value of the β-emission energy of $^{32}$P.

One reason radioactive phosphorus has received relatively little attention for targeted radiotherapy applications has been the difficulty of linking it to targeting proteins. Most of the methods currently known are non-specific and slow, and do not efficiently incorporate radionuclide into the targeting protein.

Another reason that radioactive phosphorus has received relatively little attention for radioimmunotherapy, is the rapid dephosphorylation of $^{32}$P in human serum. It has been proposed that enhanced serum stability of $^{32}$P in, e.g., the kemptide sequence can be achieved by modifying the primary sequence of receptor peptides.

One very general method of labeling proteins with $^{32}$P is simply to incubate the protein with α-$^{32}$P-labeled nucleoside triphosphates. Schmidt et al., FEBS Lett. 194:305 (1986). The mechanism for the labeling reaction is unknown. The method is slow and gives only poor incorporation of label (less than 1% of the protein molecules are labeled), and is thus too inefficient for therapeutic use.

A second general method of $^{32}$P labeling is to incubate Proteins with [γ-$^{32}$P]ATP or H$_3$$^{32}$PO$_4$ in the Presence of chromium ions. Hwang et al., Biochim. BioPhys. Acta 882:331 (1986). This method is relatively rapid, but gives an unknown level of label incorporation and also leaves toxic chromium ions bound to the proteins, which would be therapeutically unacceptable.

A third general method is the use of $^{32}$P-diphenylphosphinothionyl chloride as a reactive labeling compound. De Boer et al., Clin. Exp. Immunol. 3:865 (1968). This reagent is thought to react non-specifically with lysine residues in proteins to form a highly stable conjugate, but approximately 50% of the radioactivity also associates non-covalently with the labeled protein. Although this method allows labeling of proteins to high specific activity, the labeling agent is only poorly water soluble, and to achieve good labeling yields large excesses of reagent must be used, wasting relatively large amounts of hazardous radioactive materials.

A less general method of $^{32}$P labeling is the use of periodate-oxidized [α-$^{32}$P]ATP to affinity-label proteins containing an ATP-binding site. Clertant et al., J. Biol. Chem. 257:6300 (1982). Because many targeting proteins which are of therapeutic interest, in particular antibodies, do not contain ATP-binding sites this method is therefore of little general utility.

A more recent method, intended for labeling antibodies for radiotherapy, involves the chemical conjugation of protein kinase substrate peptides to antibodies. Foxwell et al., Brit. J. Cancer 57:489 (1988). The conjugates are labeled by treatment with [γ-$^{32}$P]ATP in the presence of the catalytic subunit of cAMP-dependent protein kinase (protein kinase A, PKA), which transfers $^{32}$P-phosphate to a serine residue in the substrate peptide. This method showed differences in the β-phase half-life between the $^{32}$P-labeled antibody and a corresponding $^{131}$-I-labeled antibody, and also high $^{32}$P uptake in the bone of animals injected with the labeled antibody. Creighton et al., "The development of $^{32}$P technology for radioimmunotherapy" in MONOCLONAL ANTIBODIES 2. APPLICATIONS IN CLINICAL ONCOLOGY. A.A. Epenetos, ed., Chapman and Hall, (1993) pp. 103–109. These results indicate in vivo instability of the label, presumably due to the action of protein phosphatases which are ubiquitous in eukaryotic cells.

Recently, Leung et al., Cancer Res. 55:5968s (1995) successfully expressed a hMN-14Fab'-kemptide fusion protein that can be enzymatically phosphorylated with $^{32}$P by bovine protein kinase. The kemptide sequence was attached at the C-terminus of the human IgG1 hinge region and phosphorylation of the sequence did not affect the immunoreactivity of the fusion antibody, thus resolving the problem of non-site-specific conjugation associated with the chemically linked kemptides.

While these methods serve well to phosphorylate the protein, the attached $^{32}$P was rapidly dephosphorylated from the kemptide sequence in human serum, probably by serum phosphatases. Although enhanced serum stability of the $^{32}$P in the kemptide sequence can be achieved by modifying the primary sequence of receptor peptides, it is always at the expense of reduced ease of phosphorylation by protein kinases. While these findings have discouraged the use of kemptide sequence as the substrate from $^{32}$P labeling, they nevertheless demonstrated the feasibility of enzymatically labeling antibodies and antibody fragments engineered with the appropriate phosphorylation peptide sequences.

pawson (U.S. Pat. No. 5,352,660) and pawson et al. (U.S. Pat. No. 5,667,980) disclose methods for assaying a medium for the presence of a substance that affects an SH2-phosphorylated ligand regulatory system. The patents also disclose a SH2-phosphorylated ligand complex which is capable of interacting with an SH2 like domain or subdomain thereof. pawson and pawson et al. fail to recognize the ability of the SH2 domain to inhibit in vivo dephosphorylation.

It is apparent therefore, that $^{32}$P- and $^{33}$P-labeling proteins are greatly desired for in vivo therapeutic and diagnostic usage. In particular, substances wherein the $^{32}$P or $^{33}$P label is stable in vivo, are not readily dephosphorylated, and which do not compromise the binding abilities of these proteins are needed.

SUMMARY OF THE INVENTION

A radiotherapeutic agent precursor comprising a protein selected from the group consisting of:

| | |
|---|---|
| X-Y-L-SH2 | (I); |
| X-SH2-L-Y | (II); |
| Y-X-SH2 | (III); | and (IV)

wherein X is a targeting peptide, Y is a phosphorylation peptide, L is a flexible linker and SH2 represents an SH2 domain. The invention also relates to $^{32}$P or $^{33}$P radiolabeled agents of formulae (I')–(IV'):

| | |
|---|---|
| X-Y'-L-SH2 | (I'); |
| X-SH2-L-Y' | (II'); |
| Y-X-SH2 | (III'); | and (IV')

wherein X is a targeting peptide, Y' is a phosphorylation peptide, L is a flexible linker and SH2 represents an SH2 domain; wherein said phosphorylation peptide is radiolabeled with $^{32}$P or $^{33}$P.

DETAILED DESCRIPTION OF THE INVENTION

The present invention relates to radiotherapeutic agent precursors of the following formulae:

| | |
|---|---|
| X-Y-L-SH2 | (I); |
| X-SH2-L-Y | (II); |
| Y-X-SH2 | (III); | and (IV)

wherein X is a targeting peptide, e.g., an antibody, Y is a phosphorylation peptide, L is a flexible linker, preferably a peptide linker and SH2 represents an SH2 domain. The radiotherapeutic agents are proteins radiolabeled with $^{32}$P or $^{33}$P which contain a SH2 domain and have the following formula:

| | |
|---|---|
| X-Y'-L-SH2 | (I'); |
| X-SH2-L-Y' | (II'); |
| Y-X-SH2 | (III'); | and (IV')

wherein X is a targeting peptide, Y' is a phosphorylation peptide, L is a [flexible] linker and SH2 represents an SH2 domain; wherein said phosphorylation peptide is radiolabeled with $^{32}$P or $^{33}$P.

Figure 1:
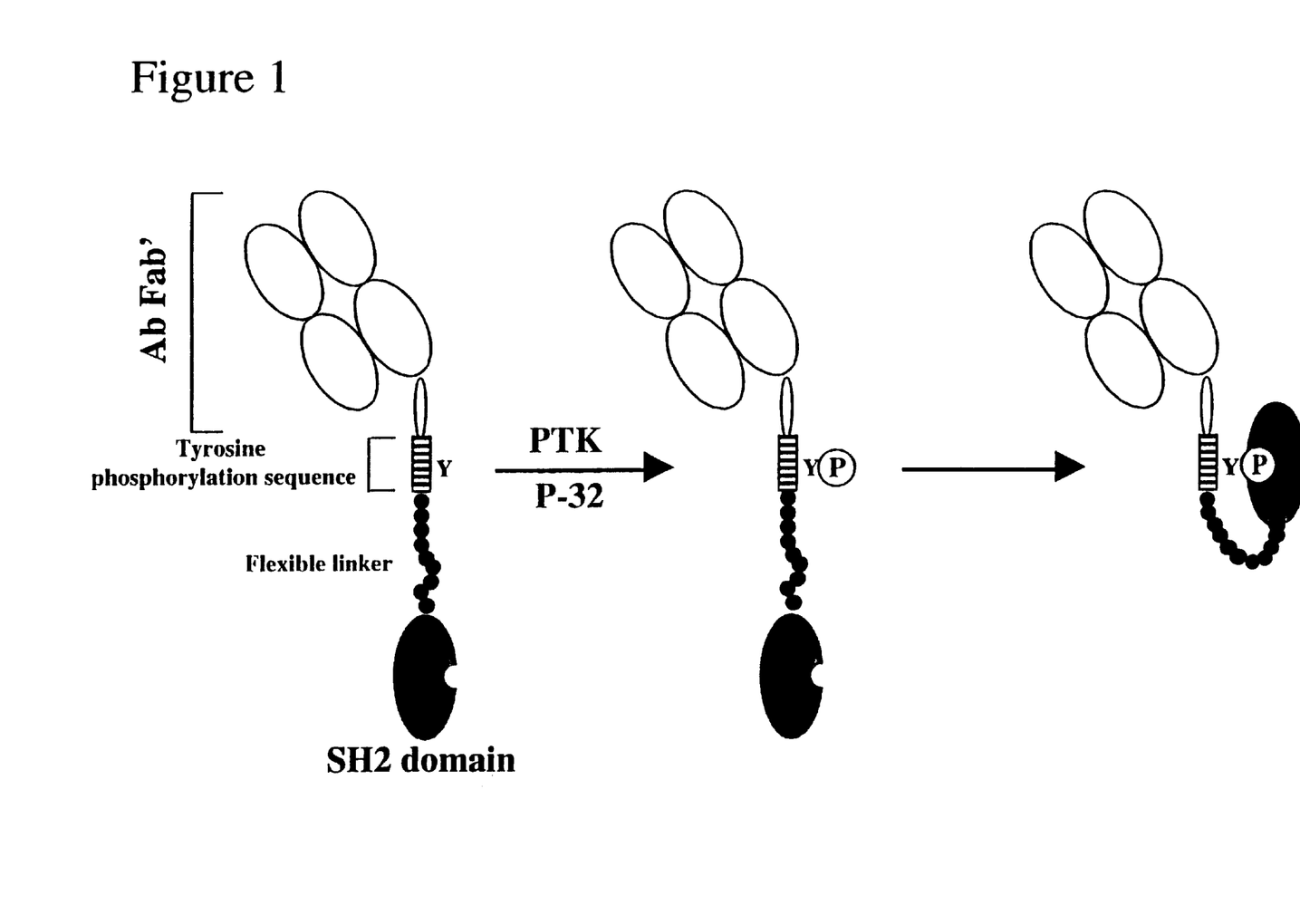
FIG. 1 shows one embodiment of the invention, wherein an antibody fragment is linked to a tyrosine phosphorylation peptide sequence which is linked to a flexible protein linker that in turn is linked to an SH2 domain.
Figure 2:
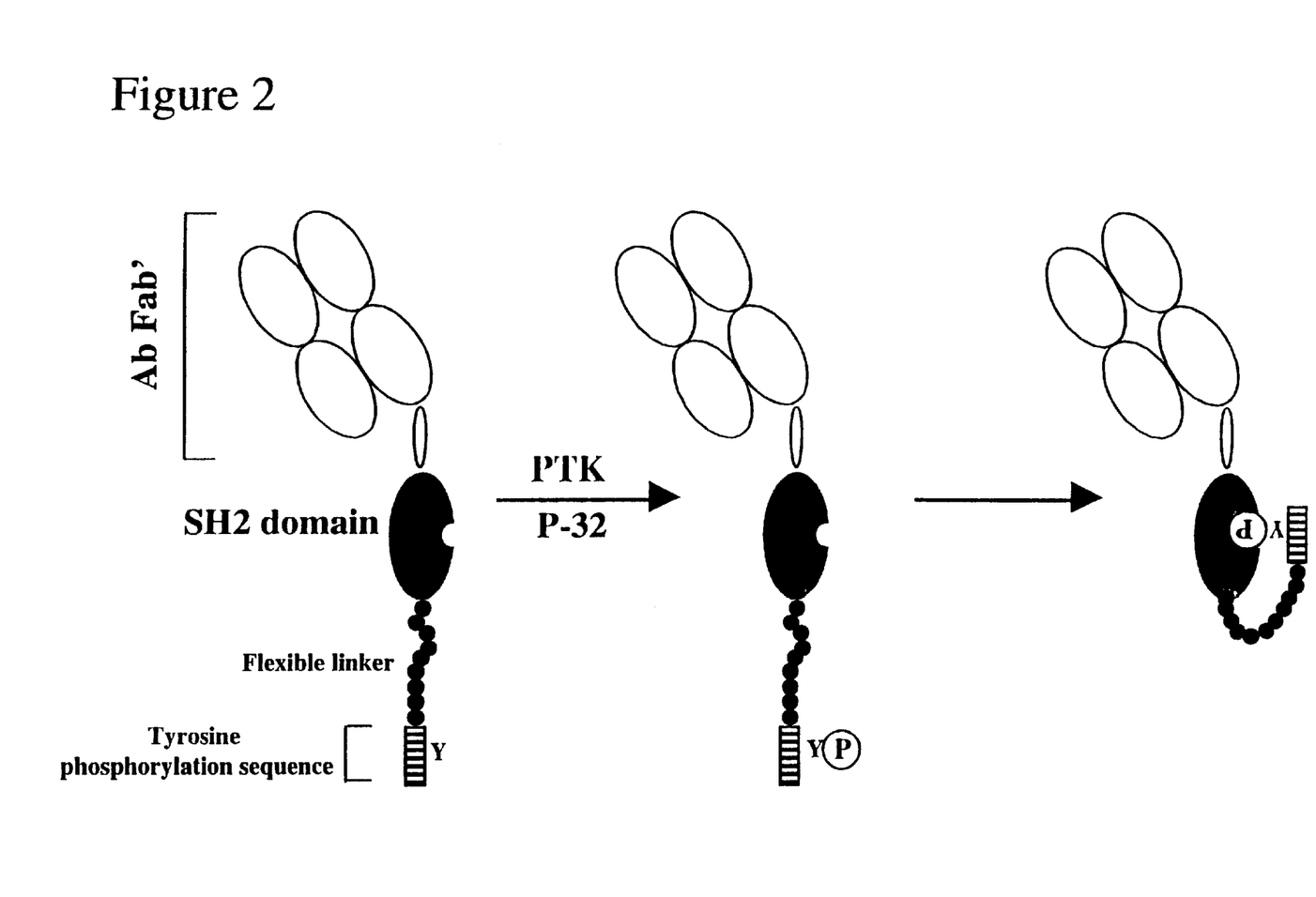
FIG. 2 shows an alternative embodiment of the invention, wherein an antibody fragment is linked to an SH2 domain which is linked to a flexible protein linker which in turn is linked to a tyrosine phosphorylation peptide sequence.

In the present invention, an intact antibody, an antibody, fragment, or another peptide targeting/recognition moiety is linked to a tyrosine phosphorylation peptide sequence, which optionally contains a flexible linker moiety, which is linked to a SH2 domain. Alternatively, the intact antibody, antibody fragment or other peptide targeting/recognition moiety is linked to an SH2 domain, which is optionally bonded to a flexible linker, which in turn is linked to a phosphorylation peptide sequence. The resultant radiolabeled agent, after kinase catalyzed radiophosphorylation, is stable in vivo, i.e., the compound is protected from enzymatic dephosphorylation by incorporation of the SH2 domain. The labeled targeting proteins bind specifically to disease cells or tissue, which are killed by the radiation from the $^{32}$P or $^{33}$P The invention also includes pharmaceutical compositions comprising an effective amount of at least one of the $^{32}$P or $^{33}$P-radiolabeled agents of the invention, in combination with a pharmaceutically acceptable sterile vehicle, as described, for example, in Remingtons' pharmaceutical Sciences; Drug Receptors and Receptor Theory, 18th ed., Mack publishing Co., Easton, Pa. (1990).

The present invention also includes methods of treating a tumor or an infectious lesion comprising administering to a patient in need thereof at least one of the $^{32}$P- or $^{33}$P-radiolabeled agents of the invention, in combination with a pharmaceutically acceptable sterile vehicle. Some areas of interest include tumor treatment and treatment of lesions which include, but are not limited to, infectious lesions of the breast, colon and rectum, prostate, ovary and testes; pathological lesions affecting the major organs of the chest, abdomen and pelvis, as well as the skin; and cardiovascular lesions, such as, a myocardial infarct, atherosclerotic plaque, clot, thrombosis, pulmonary embolism; inflammatory lesions and hyperplasia.

The present invention provides targeting proteins containing an SH2 domain with at least one peptide sequence that is a substrate for the protein kinase. Treatment of the targeting protein which contains a phosphorylation peptide sequence and an SH2 domain with a protein kinase and a $^{32}$P- or $^{33}$P- labeled phosphate donor transfers $^{32}$P- or $^{33}$P-phosphate efficiently and specifically to a predetermined amino acid in the kinase substrate sequence, thereby radiolabeling the targeting protein.

The invention further includes kits for labeling the targeting proteins containing a phosphorylation peptide and an SH2 domain which are convenient and easy to use in a clinical environment.

The antibody used in the present radiotherapeutic agents can be an antibody or an antibody fragment. The antibody or fragment, preferably is a chimeric, humanized or human antibody.

In accordance with one embodiment, the antibody comprises monoclonal antibodies or antibody fragments. In accordance with another embodiment, the antibody comprises humanized antibodies or antibody fragments. Monoclonal antibodies (MAb) are usually mouse proteins, and they are not identical to human antibodies. Hence, antibodies from a mouse, when injected into a patient, will eventually be cleared from circulation as being recognized as foreign proteins. Both chains of the antibody molecule can be divided into variable and constant regions. In each antibody, the variable regions differ from one antibody to the next. This is the region that binds the antigen. The constant region of the antibody is the same among antibodies of the same type. The basic structure of a mouse Mab resembles that of a human antibody. However, there are numerous differences between amino acid sequences of the antibodies from the two species. These sequence differences account for the immunogenicity of mouse MAbs in humans. A chimeric Mab is constructed by ligating the cDNA fragment encoding the mouse light variable and heavy variable domains to fragment encoding the C domains from a human antibody. Because the C domains do not contribute to antigen binding, the chimeric antibody will retain the same antigen specificity as the original mouse Mab but will be closer to human antibodies in sequence. Chimeric Mabs still contain some mouse sequences, however, and may still be immunogenic. A humanized Mab contains only those mouse amino acids necessary to recognize the antigen. This product is constructed by building into a human antibody framework the amino acids from the mouse complementarity determining regions. Human antibodies can be raised in transgenic animals by conventional recombinant techniques.

Antibody fragments for use in the invention can be multivalent, divalent or monovalent, including bispecific fragments.

A multivalent antibody fragment, as used herein, encompasses a chemical combination of fragments having specificity to more than one type of tumor-associated antigen.

A divalent antibody fragment, as used herein, encompasses fragments of antibodies, e.g., F(ab')2, which retain a disulfide cross-link between the two parts of the antibody.

A monovalent antibody fragment, as used herein, encompasses Fab' and Fab fragments, normally obtained by cleavage of bivalent fragments or intact immunoglobulin. Fab' antibody fragments are normally and conveniently made by reductive cleavage of $F(ab')_2$ fragments, which themselves are normally made by pepsin digestion of intact immuno-globulin. Fab antibody fragments can be made by papain digestion of intact immuno-globulin, under reducing conditions, or by cleavage of $F(ab)_2$ fragments which result from careful papain digestion of whole Ig. parham et al., J. Immunol. Methods, 53:133–173, 1982, and Boguslawski et al., J. Immunol. Methods, 120:51–56, 1989, show papain digestion of murine monoclonal $IgG_1$ to $F(ab)_2$. Activation of the papain with thiol, followed by removal of the thiol prior to cleavage, permits cleavage of those immunoglobulins having the papain cleavage site below at least one disulfide bond to occur without further cleavage of the bivalent fragment.

It will be appreciated, however, that monovalent fragments can also include any fragments retaining the hypervariable, antigen-binding region of an immunoglobulin and having a size similar to or smaller than a Fab' fragment. This will include genetically engineered and/or recombinant proteins, whether single-chain or multiple-chain, which incorporate an antigen binding site and otherwise function in substantially the same way as natural monovalent immunoglobulin fragments. Also included as the targeting agent is a peptide, e.g., somatostatin.

The therapeutic agents used in the invention may also encompass other targeting proteins which are used to preferentially bind to cells and tissues which are associated with a disease state and, by killing these cells or tissues, alleviate the disease state. This binding occurs to complementary molecules and structures associated with or expressed on the surface of the diseased cells or tissue, which preferably are not associated with or expressed on the surface of healthy cells. More typically the complementary moieties will be present on healthy cells, but to a lesser extent than is observed in the disease state. For example, many myelomas show large increases in expression of the interleukin 6 (IL-6) receptor compared to normal tissue. $^{32}$P-labeled proteins targeted at the IL-6 receptor will bind preferentially to myeloma cells, leading to a high effective concentration of $^{32}$P and causing preferential cell killing at the site of the tumor. Another example is carcinoembryonic antigen (CEA) which is highly expressed on the surface of many tumors. A $^{32}$P-labeled antibody or antibody fragment which binds to CEA will cause preferential cell killing at the tumor site.

It has been shown that the kemptide peptide sequence has been found to be useful as a substrate for enzymatic addition of $^{32}$P In addition to the kemptide sequence, there are other sequences, found in proteins involved in the signal transduction pathway, that can be used as substrates for enzymatic addition of $^{32}$P. For example, protein tyrosine kinases (PTKs) such as JAK1, JAK2, or Tyk2 can enzymatically attach a phosphorus at Y466 (shown bolded and underlined) of the IFNaRI cytoplasmic sequence (SEQ ID NO: 22) RCIN<u>Y</u>VFFPSLKPSS. In a CD45 molecule, binding of the phosphorylated tyrosine with the intramolecular C-terminal SH2 domain protects the phosphorylated sequence from dephosphorylation by phosphatase. An Ab fusion protein containing a phosphorylation sequence for pTK phosphorylation, when linked to a corresponding SH2 domain via a flexible peptide hinge, can therefore be labeled with $^{32}$P at the tyrosine of the phosphorylation sequence by the appropriate PTK, and the phosphorylated tyrosine, upon rapid recognition and binding by the C-terminal SH2 domain, will be stabilized and protected from dephosphorylation by serum phosphatase. The phosphorylation peptide may encompass a recombinant fusion protein, a substrate for at least one serine/threonine-specific or tyrosine-specific protein kinase. preferred kinases used in the present invention include a substrate for at least one serine/threonine-specific or tyrosine-specific protein kinase, a substrate for at least one protein kinase chosen from the group consisting of: bovine heart protein kinase, protein kinase A, protein kinase C, calcium/calmodulin-dependent protein kinase, casein kinase II, phosphorylase kinase, EGF-receptor kinase, insulin receptor kinase, src, abl, lck, fyn, yes, lyn, JAK1, JAK2, tyk2, MAP and P72$^{syk}$. Preferred substrate sequences for phosphorylation include a protein sequence as detailed in TABLE 1 from Songyang et al., *Cell* 72:767–778 (1993).

TABLE 1a

| SH2 Domain | Binding Sites in Proteins | Protein |
| --- | --- | --- |
| Src family SH2 | PQEGLYNELQKDKMAEAYSEIGM | Human CD3 δ chain |
| | NLSKRYEEIYL | Human Rb-associated rb 110 |
| | EGDEIYEDLMR | Human vuv oncogene |
| | ASEQGYEEMRA | Human ErbB3 |
| | ELQDDYEDMME | Human red cell band 3 |
| | AACVVYEDKSH | Human T cell CD7 |
| | PIASKYEDMYP | Human G2 cyclin b |
| Abl SH2 | EEEGEGYEEPDS | Human CD19 |
| | SQDGSGYENPED | Human CD19 |
| | DDGEITYENVQV | Human CD72 |
| | DRRERDYTNLPS | Human colony-stimulating factor 1 receptor |
| | PEPPPVYTNLSS | Human JunB |
| | EFAGFSYTNPEF | Human protein kinase Cβ1 |
| Crk SH2 | AKILKQYDHPNI | Human fer tyrosine kinase |
| Nck SH2 | PLCHSDYDEDDY | Human cell cycle gene |
| Sem-5 SH2 | FLPVPEYINQSV | Human EGF Receptor |

TABLE 1a-continued

| SH2 Domain | Binding Sites in Proteins | Protein |
| --- | --- | --- |
| | AVGNPEYLNTVQ | Human EGF Receptor |
| | LFDDPSYVNVQN | Human SHC |
| p85 N-terminal SH2 | ESDGGYMDMSKDESVDYVPMLD | Human PDGF receptor β |
| | DSTNEYMDMKP | Human c-Kit |
| PLC-γ-C-terminal SH2 | NEGDNDYIIPLP | Human PDGF receptor β |
| STAT 1/2 SH2 | RCINYVFFPSLKPSS | Human IFNaR1 cytoplasmic sequence |

The peptide linker, represented by L in formulae (I) and (II), is a flexible protein which may be obtained from an antibody and may include, e.g., (SEQ ID NO: 23) (GGGS)$_4$, IgG$_3$ hinge, and IgG$_1$ hinge. The linkers must be long and flexible enough to allow the SH2 domain to make a 180 degree turn and fold back on the phosphorylated substrate. The examples are only illustrative of the principle that any linker which facilitates the intramolecular folding back of SH2 onto the phosphorylated sequence can be used. The linkers can be in the form of a fusion protein and chemical linkers. (GGGS)$_4$ (SEQ ID NO: 23) is a preferred linker because it is a long hinge with multiple -SH groups. It allows the dimerization of antibody fragments and confers the needed flexibility for the SH2/phosphopeptide interactions. IgG$_1$ hinge is similarly preferred although IgG$_1$ hinge is not as long and flexible as IgG$_3$ hinge. preferred chemical linkers include imidoesters (e.g., dimethylsuberimidate.HCL) homobifunctional NHS-ester cross linkers (e.g., disuccinimidyl suberate), NHS-ester-maleimide heterobifunctional cross-linke5rs (e.g., bismaleimidohexane), puridyldithiol cross-linkers (e.g., succinimidyl 6-[3-(2-pyridyldithio)-propionamido]hexanoate).

The term SH2 domain refers to a sequence which is substantially homologous to an Src homology region 2. The Src homology region is a noncatalytic domain of approximately 100 amino acids which was originally identified in the Vfps and Vsrc cytoplasmic tyrosine kinases by virtue of its effect on both catalytic activity and substrate phosphorylation. The SH2 domain used in the present invention may encompass a P85 N-terminal SH2, a P85 C-terminal SH2, a PLC-γ C-terminal PLC-γ N-terminal SH2, a SHPTP2 N-terminal SH2, a Src family SH2, a Abl SH2, a Crk SH2, a Nck SH2, STAT1/2, CD45 SH2 and Sem-5 SH2 domain.

For the purposes of chemical and enzymatic reactivity, $^{32}$P and $^{33}$P labeled molecules behave identically. It will be understood therefore that reference hereafter to labeling with $^{32}$P will also encompass $^{33}$P.

A. Methods for preparing $^{32}$P-Labeled Compounds Containing an SH2 Domain.

The labeled proteins of the current invention can be derived from any protein which binds with specificity to molecules or tissue structures that are implicated in diseases. Examples of such targeting proteins include, but are not limited to: monoclonal antibodies and antigen-binding fragments of monoclonal antibodies; lymphokines, cytokines, and peptide growth factors; and lymphokine or cytokine receptor antagonists.

The [antibody-phosphorylation peptide-linker-SH2 domain] fusion protein, encompassing any intact antibody, antibody fragment or peptide targeting/recognition moiety, coupled to a PTK phosphorylation sequence or a peptide analog of similar structure useful as a $^{32}$P carrier moiety and linked via a flexible peptide linker to a corresponding SH2 domain, is constructed using molecular biology techniques, such that the peptide-linker-SH2 structure is attached site specifically at the C-terminus, distal from the antigen binding site. A conjugate of defined structure, having a 1:1 ratio of targeting agent to $^{32}$P carrier peptide, and ultimately to $^{32}$P, is thus obtained.

The various conjugates comprising the target vector-PTK phosphorylation peptide-linker SH2 domain are made using methods which are illustrated by the example below, which describes the construction and use of a protein comprising an antibody fragment-PTK phosphorylation peptide-linker-SH2 domain.

hMN-14 is a humanized MAb of the IgG1 sub-type raised against CEA. Bacterial expression vector, hMN14pBEV, for the secretory expression of antibody fragments, Fab' or F(ab')$_2$, has been constructed by Leung et al. (Cancer Research 55:5968s 1995). The vector contains a dicistronic gene comprised of the heavy chain Fd, the heavy chain portion of an Fab fragment, encoding DNA fused to its hinge region and the light chain encoding DNA. The expression of the genes is driven by an isopropyl-thio-β-D-galactoside (IPTG) inducible LacZ promoter. Secretion of the functional ab' fragment is accomplished by transforming the expression vector into an *E coli* mutant (BMH71-18mutS), growing the transformants overnight at 37° C. in supplemented with 55 mM glucose and 100 μg/ml of ampicillin, and inducing expression with 1–5 mM of IPTG at 37° C. over 24 hours. At downstream regions of the DNA encoding the Fd-hinge fragment, convenient restriction sites are introduced to facilitate subcloning. The DNA sequence (~620 nucleotides) encoding the IFNaRI cytoplasmic domain sequence RCIN YVFFPSLKPSS linked to the SH2 domain sequence of STAT2 (amino acid length 549–672) via a flexible linker, is constructed separately by a combination of gene-synthesis and polymerase chain reaction. Appropriate restriction sites or compatible staggered ends are introduced at the 5' and 3' ends of the DNA to facilitate directional cloning.

A 62 nucleotide oligomer complementary to the DNA encoding the sequence (SEQ ID NO: 24) HTCP-PCPRCINYVFFPSL is synthesized. A DraI and a BglII site are introduced at a region corresponding to the C-terminus of the peptide. The sequence HTCPPCP represents the last 7 amino-acids of the hMN14 hinge region, while the other 11 residues represent the N-terminal part of the PTK phosphorylation sequence.

Method of Administration

Generally, the dosage of administered $^{32}$P-labeled protein will vary depending upon such factors as the patient's age, weight, height, sex, general medical condition, and previous medical history. Typically, it is desirable to provide the recipient with a dosage of labeled protein which is in the range of from about 1 pg/kg to 10 mg/kg (amount of agent/body weight of patient), although a lower or higher dosage may also be administered.

For therapeutic applications, about 1–50 milligrams of $^{32}$P-labeled protein will be administered, normally daily for a period of several days.

Administration of labeled proteins to a patient can be intravenous, intraarterial, intraperitoneal, intramuscular, subcutaneous, intrapleural, intrathecal, by perfusion through a regional catheter, or by direct intralesional injection. When administering the protein by injection, the administration may be by continuous infusion, or by single or multiple boluses.

The labeled proteins of the present invention can be formulated according to known methods to prepare pharmaceutically useful compositions, whereby labeled proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, REMINGTON'S PHARMACEUTICAL SCIENCES, 18th Ed. (1990).

For purposes of therapy, a $^{32}$P-labeled protein and a pharmaceutically acceptable carrier are administered to a patient in a therapeutically effective amount. A combination of a $^{32}$P-labeled protein and a pharmaceutically acceptable carrier is said to be administered in a "therapeutically effective amount" if the amount administered is physiologically significant. An agent is physiologically significant if its presence results in a detectable change in the physiology of a recipient patient. A targeted therapeutic agent is therapeutically effective if it delivers a higher proportion of the administered dose to the intended target than accretes at the target upon systemic administration of the equivalent untargeted agent.

To be therapeutically effective the labeled protein and carrier may need to be administered in combination with other therapeutic agents or as part of a broader treatment regimen. physicians now are currently of the opinion that the effectiveness of targeted therapeutics can often be greatly increased when used in a combination therapy approach. For example, high-dose radioimmunotherapy for B-cell lymphomas, which causes severe hematologic toxicity when used alone, has been shown to be highly effective when used in combination with autologous bone marrow reinfusion. press et al., "Treatment of Relapsed B Cell Lymphomas with High Dose Radioimmunotherapy and Bone Marrow Transplantation" in CANCER THERAPY WITH RADIOLABELED ANTIBODIES, Goldenberg, Ed. (CRC press, Boca Raton, 1995) ch. 17. In another example a five-fold enhancement of tumor uptake of a radiolabeled antibody is observed when the tumor is preirradiated. Leichner et al., *Int. J. Radiat. Oncol. Biol. phys.* 14:1033 (1987). Mechanisms which have been shown to have the potential for improving the clinical efficacy of radioimmunotherapy are also discussed in DeNardo et al., "Overview of Obstacles and Opportunities for Radioimmunotherapy of Cancer" in CANCER THERAPY WITH RADIOLABELED ANTIBODIES, Goldenberg, Ed. (CRC press, Boca Raton, 1995) ch. 11. Efforts to develop such combination protocols, as well as to investigate dose-limiting side effects and to potentiate and amplify targeting, uptake, and beneficial side effects, are underway in many laboratories and hospitals and are expected to further enhance the utility of targeted therapeutic agents.

Additional pharmaceutical methods may be employed to control the duration of action of the labeled protein in a therapeutic application. Controlled release preparations can be prepared through the use of polymers to complex or adsorb a protein. For example, biocompatible polymers include matrices of poly(ethylene-co-vinyl acetate) and matrices of a polyanhydride copolymer of a stearic acid dimer and sebacic acid. Sherwood et al., *Bio/Technology* 10:1446–1449 (1992). The rate of release of a $^{32}$P-labeled protein from such a matrix depends upon the molecular weight of the protein, the amount of protein within the matrix, and the size of dispersed particles. Saltzman et al., *Biophysical. J*. 55:163–171 (1989); and Sherwood et al., supra. Other solid dosage forms are described in REMINGTON'S PHARMACEUTICAL SCIENCES, 18th Ed. (1990).

What is claimed is:

1. A radiotherapeutic agent comprising a $^{32}$P or $^{33}$P radiolabeled protein selected from the group consisting of:

X-Y'-L-SH2(I);
X-SH2-L-Y'(II);

(IV)

wherein X is a targeting peptide, Y' is a phosphorylation peptide, L is a linker and SH2 represents an SH2 domain; wherein said phosphorylation peptide is radiolabeled with $^{32}$P or $^{33}$P and wherein the linker is long and flexible enough to allow the SH2 domain to make a turn and fold back on the phophorylated substrate.

2. The radiotherapeutic agent of claim 1, wherein said targeting peptide is an intact antibody or an antibody fragment.

3. The radiotherapeutic agent of claim 1, wherein said phosphorylation peptide is a PTK phosphorylation sequence or a peptide analog of a PTK phosphorylation sequence.

4. The radiotherapeutic agent of claim 1, wherein said linker is a peptide linker or chemical linker.

5. The radiotherapeutic agent of claim 4, wherein said linker is a (SEQ ID NO:23) (GGGS)$_4$, an IGI$_3$ hinge region, or an IgG hinge region.

6. The radiotherapeutic agent of claim 4, wherein said chemical linker is selected from the group consisting of imidoesters, homobifunctional NHS-ester cross linkers, NHS-ester-maleimide heterobifunctional cross-linkers, and puridyldithiol cross-linkers.

7. The radiotherapeutic agent of claim 4, wherein said chemical linker is selected from the group consisting of dimethylsuberimidate. HCL, disuccinimidyl suberate, bismaleimidohexane, and succinimidyl 6-[3-(2-pyridyldithio)-propionamido]hexanoate.

8. The radiotherapeutic agent of claim 2, wherein said intact antibody is a humanized monoclonal antibody.

9. The radiotherapeutic agent of claim 2, wherein said antibody fragment is selected from the group consisting of Fab', F(ab')$_2$, Fab, Fv, and sFv.

10. The radiotherapeutic agent of claim 1, wherein said SH2 domain is selected from the group consisting of p85 N-terminal SH2, P85 C-terminal SH2PLC-γ C-terminal SH2, PLC-γ N-terminal SH2, SHPTP2 N-terminal SH2, Src family SH2, Abl SH2, Crk SH2, Nck SH2, STAT1/2, CD45 SH2, and Sem-5 SH2.

11. A pharmaceutical composition comprising an effective amount of at least one radiotherapeutic agent according to claim 1, in combination with a pharmaceutically acceptable sterile vehicle.

12. A radiotherapeutic agent precursor comprising a protein selected from the group consisting of:

X-Y-L-SH2 (I);

X-SH2-L-Y (II);

and (IV)

wherein X is an targeting peptide, Y is a phosphorylation peptide, L is a linker and SH2 represents an SH2 domain, and wherein the linker is long and flexible enough to allow the SH2 domain to make a turn and fold back on the phophorylated substrate.

13. The radiotherapeutic agent precursor of claim 12, wherein said targeting peptide is an intact antibody or an antibody fragment.

14. The radiotherapeutic agent precursor of claim 12, wherein said phosphorylation peptide is a PTK phosphorylation sequence or a peptide analog of a PTK phosphorylation sequence.

15. The radiotherapeutic agent precursor of claim 12, wherein said linker is a (SEQ ID NO: 23) (GGGS)$_4$, and IgG$_3$ hinge region, or an IgG hinge region.

16. The radiotherapeutic agent precursor of claim 12, wherein said antibody fragment is selected from the group consisting of Fab', F(ab')$_2$, Fab, Fv, and sFv.

17. The radiotherapeutic agent precursor of claim 12, wherein said SH2 domain is selected from the group consisting of P85 N-terminal SH2, P85 C-terminal SH2, PLC-γ C-terminal SH2, PLC-γ N-terminal SH2, SHPTP2 N-terminal SH2, Src family SH2, Abl SH2, Crk SH2, Nck SH2, STAT1/2, CD45 SH2, and Sem-5 SH2.

18. The radiotherapeutic agent precursor of claim 12, wherein said linker is a peptide linker or chemical linker.

19. The radiotherapeutic agent of claim 18, wherein said linker is a (GGGS)$_4$, an IgI$_3$ hinge region, or an IgG hinge region.

20. The radiotherapeutic agent of claim 18, wherein said chemical linker is selected from the group consisting of imidoesters, homobifunctional NHS-ester cross linkers, NHS-ester-maleimide heterobifunctional cross-linkers, and puridyldithiol cross-linkers.

21. The radiotherapeutic agent of claim 18, wherein said chemical linker is selected from the group consisting of dimethylsuberimidate.HCL, disuccinimidyl suberate, bismaleimidohexane, and succinimidyl 6-[3-(2-pyridyldithio)-propionamido]hexanoate.

22. A kit for use in preparing a radiotherapeutic agent, comprising:

a radiotherapeutic agent precursor according to claim 12; and a phosphorylation enzyme selected from the group consisting of JAK1, JAK2, and Tyk2.

23. A method for treating a tumor or an infectious lesion in a patient comprising administering an effective amount of a radiotherapeutic agent wherein said radiotherapeutic agent comprises a $^{32}$P or $^{33}$P radiolabeled protein selected from the group consisting of:

X-Y-L-SH2 (I);

X-SH2-L-Y (II);

Y-X-SH2 (III);

and (IV)

wherein X is a targeting peptide, Y is a phosphorylation peptide, L is a flexible linker and SH2 represents an SH2 domain; wherein said phosphorylation peptide is radiolabeled with $^{32}$P or $^{33}$P.

24. The method of claim 23, wherein the radiotherapeutic agent is administered by intravenous injection.

25. The method of claim 23, further comprising administering a second antibody to clear circulating non-targeted radiotherapeutic agent.

* * * * *